US005859972A

United States Patent [19]
Subramaniam et al.

[11] Patent Number: 5,859,972
[45] Date of Patent: Jan. 12, 1999

[54] MULTIPLE SERVER REPOSITORY AND MULTIPLE SERVER REMOTE APPLICATION VIRTUAL CLIENT COMPUTER

[75] Inventors: Shankar Subramaniam, Urbana; Mark Stupar, Champaign; Eric Jakobsson, Urbana, all of Ill.; Curtis Jamison, Beltsville, Md.

[73] Assignee: The Board of Trustees of The University of Illinois, Urbana, Ill.

[21] Appl. No.: 662,771

[22] Filed: May 10, 1996

[51] Int. Cl.[6] ........................................... G06F 17/30
[52] U.S. Cl. ..................... 395/200.33; 707/3; 707/4; 707/10; 395/200.33; 395/200.47; 395/200.53
[58] Field of Search ..................... 395/604, 610, 395/616, 200.03, 200.08, 200.33, 200.47, 200.53; 707/4, 3, 10

[56] References Cited

U.S. PATENT DOCUMENTS

| | | | |
|---|---|---|---|
| 5,058,000 | 10/1991 | Cox et al. | 364/200 |
| 5,218,697 | 6/1993 | Chung | 395/200.6 |
| 5,375,207 | 12/1994 | Blakely et al. | 395/200 |
| 5,572,643 | 11/1996 | Judson | 395/793 |
| 5,600,833 | 2/1997 | Senn et al. | 395/601 |
| 5,604,896 | 2/1997 | Duxbury et al. | 395/200.57 |
| 5,625,816 | 4/1997 | Burdick et al. | 395/614 |
| 5,634,127 | 5/1997 | Cloud et al. | 395/680 |
| 5,640,446 | 6/1997 | Everett et al. | 379/115 |
| 5,642,337 | 6/1997 | Oskay et al. | 369/30 |
| 5,649,186 | 7/1997 | Ferguson | 395/610 |
| 5,751,957 | 5/1998 | Hiroya et al. | 395/200.33 |
| 5,754,774 | 5/1998 | Bittinger et al. | 395/200.33 |
| 5,754,841 | 5/1998 | Carino, Jr. | 395/682 |

*Primary Examiner*—Thomas G. Black
*Assistant Examiner*—Jean R. Homere
*Attorney, Agent, or Firm*—Greer, Burns & Crain, Ltd.

[57] ABSTRACT

A system and method for managing informatics in a specialty field, such as medicine, biology, and so on. A local workstation is connected to a server over a network. A user runs a browser application on the local workstation. A plurality of remote data repositories are accessible to the server. The informatics management system includes a gateway program running on the server. The gateway program receives a query request in a first format from the user over the network. The gateway program includes a query translator routine that translates the query request from the first format to a plurality of different formats. The translated query requests are sent to the remote data repositories and results are received therefrom. The gateway program includes a results translator routine that translates the results received from the remote data repositories into results in the first format and sends the results in the first format to the user's workstation. In a further aspect of the system, query results can be used as input data to analysis tools and programs. The gateway program includes a translator routine that translates the query results into input data for a remote tool or analysis program. A driver routine launches the remote analysis program. The gateway program includes a translator routine that translates the computed results from the remote analysis program into results in the first format and sends the results in the first format to the user's workstation. In one embodiment, the network is the Internet and the first format is HTML.

49 Claims, 17 Drawing Sheets

Microfiche Appendix Included
(3 Microfiche, 292 Pages)

DATABASE SELECTION

Use this form to select the database to search. The databases are grouped according to type. Limiting your search to a specific type will give you greater latitude in the number of searchable fields. Searching disparate types of databases will limit the number of searchable fields and the types of objects which can be searched for (eg, searching ACeDB and the WBG databases limits you to one type of returnable object: Documents).

---

Genome Databases: ACeDB SolGenes (Temporarily Unavailable)
Literature Databases: ⊐WBG⊐ Entrez_Medline
Sequence Databases: ⊐ PIR ⊐GenBank ⊐PDB

---

[ SUBMIT ]  [ RESET ]  [ MAIN ]

---

Report Bugs

Fig. 5A

QUERY BUILDER

This form allows you to build your query. If the type of
object you wish to have returned does not appear in the
list, consider returning to the database selection section
and reducing the number of disparate databases to be
searched.

You have selected the following databases: PIR PDB

Find all [Sequence ▼] where

⊃( [Protein  ▼] = [secretory trypsin in] ⊃) [End ▼]
⊃( [Person   ▼] = [                    ] ⊃) [End ▼]
⊃( [Person   ▼] = [                    ] ⊃) [End ▼]
⊃( [Person   ▼] = [                    ] ⊃) [End ▼]
⊃( [Person   ▼] = [                    ] ⊃) [End ▼]
⊃( [Person   ▼] = [                    ] ⊃) [End ▼]
⊃( [Person   ▼] = [                    ] ⊃) [End ▼]

[SUBMIT]  [RESET]  [MAIN]

Report Bugs

Fig. 5B

DATABASE RESULTS

Retrieving Class Sequence with Query:
Protein=secretory trypsin inhibitor

PIR Results
Query matched 20 record(s)

PDB Results
Query mathed 6 record(s)

Collective Results

> PIR pancreatic secretory trypsin inhibitor variant 4 (with
> PIR pancreatic secretory trypsin inhibitor precursor-
>     human
> PIR Synthetic E.coli alkaline phosphatase signal peptide/
>     human
> PIR trypsin (EC 3.4.21.4) precursor (with pancreatic
>     secretory
> PIR HUMAN pancreatic secretory trypsin inhibitor variant
>     3-human
> PDB (1cpa) EPIDIDYMAL RETINOIC ACID-BINDI (CHAIN A)
> PDB (1tgs) TRYPSINOGEN COMPLEX WITH PORCI (CHAIN I)
> PDB (1tgs) TRYPSINOGEN COMPLEX WITH PORCI (CHAIN Z)
> PDB (1cpb) EPIDIDYMAL RETINOIC ACID-BINDI (CHAIN A)

[VIEW OBJECTS] [VIEW SEQUENCES] [IMPORT TO WORKBENCH] [RESET] [MAIN]

Report Bugs

Fig. 5C

| Show DNA Tools | ide Protein Tool | ow Protein Sequence |

PROTEIN TOOLS

◻ PIR:TIBOA—pancreatic secretory trypsin inhibitor—bovine
◻ PIR:TIPG—pancreatic secretory trypsin inhibitor—pig
◻ PDB:1HPT_ —HUMAN PANCREATIC SECRETORY TRYPSIN
   INHIBITOR VARIANT
3
◻ PIR:TIHUA—pancreatic secretory trypsin inhibitor pre-
            cursor—human

```
Add Squence
Edit Sequence
Delete Sequence(s)
Veiw Sequence(s)
Database Search
BLASTP—Compare a PS to a PS DB
TBLASTN—Compare a PS to a PS-derived-from-NS DB
SSEARCH—Local Alignment of Protein Sequence Using the
         Smith-Waterman Algorithm
```

| form Selected Operat | lp on Selected Operati |

Report Bugs

Fig. 9A

MULTI SEQUENCE ALIGN RESULTS pancreatic secretory trypsin inhibitor-bovine
pancreatic secretory trypsin inhibitor-pig
HUMAN PANCREATIC SECRETORY TRYPSIN INHIBITOR VARIANT 3
pancreatic secretory trypsin inhibitor precursor-human Calculating pairwise alignments .........
******
Calculating epsilons \*\*\* Heuristic Multiple Alignment \*\*\*

1234                       \*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*
-------------------NILGREAKCTNEVNGCPRIYNPVCGTDGVTYSNECLLMENKERQTPVLIQK
-------------------TSPQREATCTSEVSGCPKIYNPVCGTDITYSNECVLCSENKKRQTPVLIQK
-------------------DSLGREAKCYNELNGCTYEYRPVCGTDGDTYPNECVLCFENRKRQTSILIQK
MKVTGIFLLSALALLSDSNTGADSLGREAKCYNELNGCTKIYDPCGTDGNTYPNECVLCFENRKRQTSILIQK

\*\*\*\*
SGPC
SGPC
SGPC
SGPC

--Estimated epsilon--

I=1 J-2 epsilon = 5
I=1 J-3 epsilon = 5
I=1 J-4 epsilon = 5
I=2 J-3 epsilon = 5
I=2 J-4 epsilon = 5
I=3 J-4 epsilon = 5

Elasped time= 0.053

Select Program to Pass Aligned Sequence to:

MSASHADE-Shaded PostScript Plots of Pre-Aligned Multiple Sequences

[form Selected Operat] [lp on Selected Operati] [Return] [Main]

Report Bugs

MULTIPLE SERVER REPOSITORY AND MULTIPLE SERVER REMOTE APPLICATION VIRTUAL CLIENT COMPUTER

MICROFICHE APPENDIX

This specification includes a microfiche appendix having 3 sheets of microfiche with 292 frames.

BACKGROUND OF THE INVENTION

The present invention relates to informatics management, and more particularly, the present invention relates to an informatics management system that provides a user in a specialized field with a gateway to globally access and use various remote data repositories, systems, and services that are related to the specific field.

Over the years, numerous data repositories and services have been developed and have been made accessible to serve users in various specialties and technical fields. Large data repositories have been developed and have been maintained to serve the fields of medicine, law, economics, meteorology, ecology, commerce, and the government, as well as many other fields and disciplines. These data repositories have been made available to users in these various fields or to the public-at-large via networks, online, or more recently, the Internet.

For example, in the field of medicine, data repositories have been developed and maintained for pharmaceutical information, case histories, etc. In the field of law, information databases are maintained for state and federal statutes, administrative regulations, and court decisions. Also, various data repositories have been developed by government bodies to provide population and census statistics, meteorological information, economic information, environmental information, etc.

These data repositories have been developed over many years and have been designed to address specific user needs. For these reasons, these various data repository systems have different data structures, query formats, communications protocols, and many have specialized user interfaces to permit users to access the systems.

Another example of an area in which data repositories have developed are the fields of molecular and structural biology research. Over the years, genome sequencing projects have been developed for a variety of organisms, including the nematode, yeast, and human genomes, and the first complete genome has been published. Sequence data has grown rapidly. As sequencing and structure determination projects proceed, the nature of bench work in the fields of molecular biology and structural biology change, becoming increasingly dependent upon information retrieval.

Currently, biologist researchers rely heavily upon sequence databases like GenBank, PIR, Swiss-Prot and PDB which contain sequence and structure information for all species. Computational tools like BLAST, FASTA, and GenQuest allow the researcher to access that information. Other programs like PSA, Grail, and MSA are used to analyze the sequence information held in the sequence databases. In addition, the biologist researcher uses literature databases like MEDLINE and Biosys and species-specific genetic databases like GDB, FlyBASE, and ACeDB, and sequence and structure databases like PDB. These databases vary in data content, as well as in internal structure and in internal rules and formats. While most of these sources are easily accessible online by personal computers, they are accessed by disparate query mechanisms. Therefore, the biologist researcher must understand several different query languages and formats. Also, integrating the results from these different databases is burdensome. Accordingly, there is a need for global communication of information in molecular biology.

As mentioned above, a field that includes disparate information systems is the field of medicine. The medical community has many types of informatics systems—some of which are computer-based and many of which are based on paper records. Some of the paper record systems date from early in this century. Where computer-based systems are used, they are often used for specific or narrow-scope applications. The computer-based systems that are currently used include various methodologies, such as CD-ROM's, commercial online systems of limited scope and functionality, and hundreds of individual Web-based pages.

There is a need for global communication of information in medicine. Providing global communication of information in the medical community would reduce the administrative burden borne by doctors and other medical professionals thereby allowing them to spend relatively more time on patient care.

In addition to the fields of molecular and structural biology and medicine, many other fields of specialties and disciplines face similar problems. Accordingly, there is a need for a system that enables a specialist in any particular field to access numerous available information systems related to that particular field in a global, efficient, and comprehensive manner.

The Internet has emerged as the standard computer network for users throughout the world to communicate with each other. Increasingly, users of the Internet employ browser applications, such as NCSA Mosaic, to access the World Wide Web.

Although many existing data repositories are accessible over the Internet, some are not. However, among the data repositories that are accessible over the Internet, many present unique or proprietary interfaces once the user is connected. Further, because many of the data repositories have different structures, the types of queries that a user would present to one repository might be very different from the queries that would be put to another repository. Accordingly, although much information is available over the Internet to specialists in many fields, and to the general population, much of the information is stored in dissimilar systems. Thus, a person wanting to search several of these systems must access each of them separately and organize all the received information locally after it has been downloaded.

SUMMARY OF THE INVENTION

In accordance with the present invention, there is provided a system and method for managing informatics in a specialty field, such a medicine, biology, law, economics and so on. A local workstation is connected to a server over a network. A user runs a browser application on the local workstation. A plurality of remote data repositories or remote application programs are accessible to the server. The informatics management system includes a gateway program running an the server. The gateway program receives a query request or a command request in a first format from the user over the network. The gateway program includes a query translator and/or a command translator routine that translates the request from the first format to a plurality of different formats. The translated query or command requests are sent to the remote data repositories and/or the remote application programs and results are received therefrom. The gateway program also includes a results translator routine that translates the results received from the remote data repositories and/or remote application programs into results in the first format. The gateway program sends the results in the first format to the user's workstation. In a preferred embodiment, the network is the Internet and the first format is HTML.

According to a further aspect of the present invention, the informatics management system includes a plurality of helper applications or software tools, that can be run on either the client workstation or the server, or both. The helper applications or tools are used to work with the retrieved data from the remote repositories or the remote application programs.

The informatics management system can be used various specialties, such as molecular and structural biology, medicine, law, economics, government, and so on.

BRIEF DESCRIPTION OF THE DRAWINGS

FIGS. 5A, 5B, and 5C are illustrations of three screens presented to the user during use an exemplary use of the embodiment of FIG. 2.

FIGS. 9A and 9B are illustrations of results screens in an exemplary use of an alternative embodiment of the invention.

FIG. 11 is an illustration of three screens presented to a user during another exemplary operation of the embodiment of FIG. 2.

DETAILED DESCRIPTION OF THE PREFERRED EMBODIMENTS

I. OVERVIEW OF INFORMATICS MANAGEMENT SYSTEM

Figure 1:
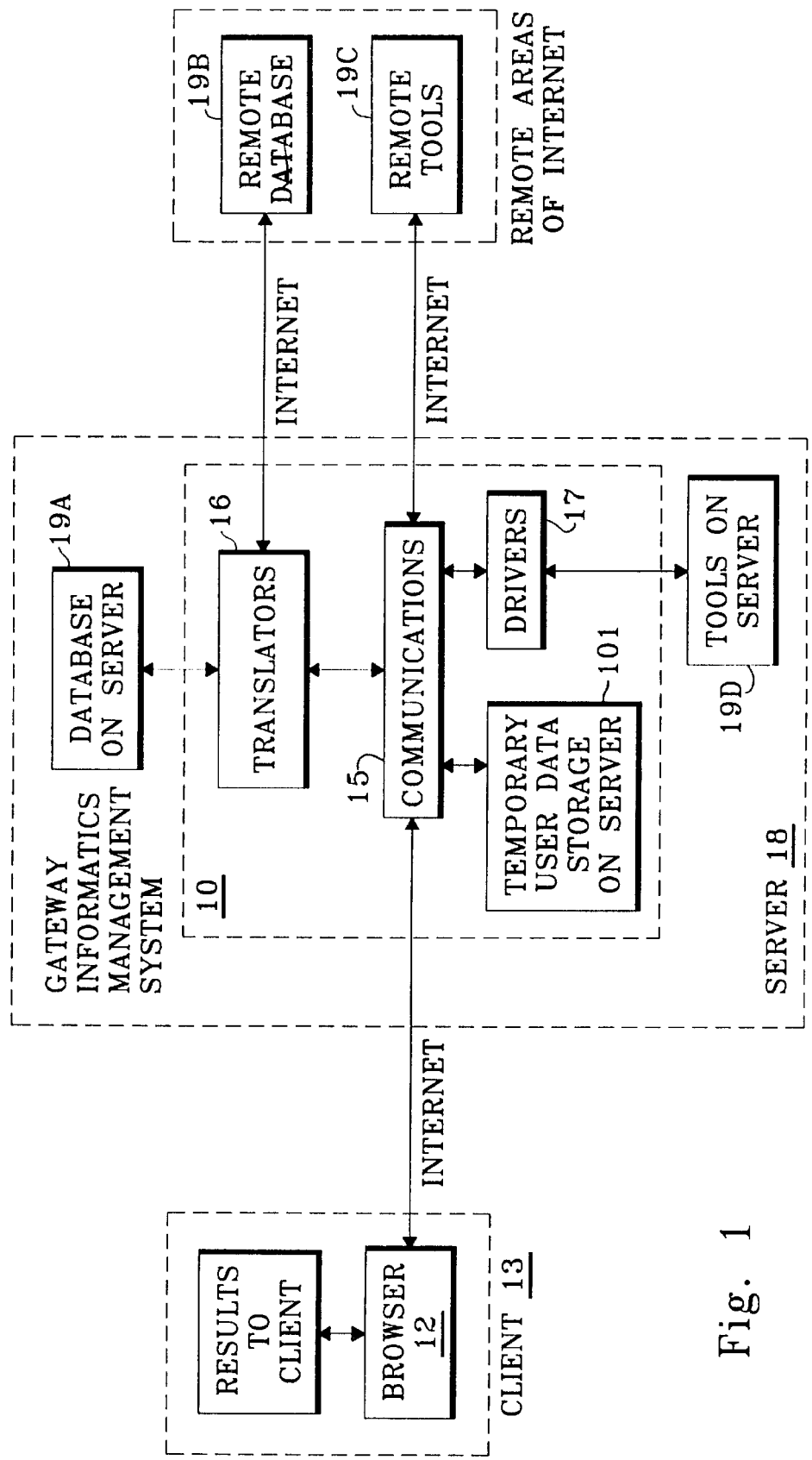
FIG. 1 is a block diagram showing a general overview of an embodiment of the present invention.

Referring to FIG. 1, there is a block diagram of a general embodiment of the present invention. The embodiment of the present invention is an informatics management system (gateway) 10 that provides a user with a WWW (World Wide Web)-based virtual computer. The gateway informatics management system 10 comprises a set of programs underlying a Web graphical browser interface. The user runs a graphical browser 12 (e.g., Netscape, Mosaic) on a client workstation 13 connected to the Internet. The gateway informatics management system program 10 resides on a server 18 connected to the Internet. The informatics management system 10 includes communications services 15, translators 16 for information repositories 19A on a server 18 and remote information repositories 19B, and drivers 17 for remote application programs (tools) 19C and application programs (tools) on the server 19D. The user runs the informatics management system 10 from the client workstation 13 with the browser 12 with conventional graphical user interface input, i.e., hypertext, pushbuttons, and filling in blanks. The informatics management system 10 draws user-specified data from the remote data repositories 19B on the Internet and from data repositories 19A on the server 18. The informatics management system 10 receives the requested results from the remote repositories 19B and the repositories 19A on the server 18 back into the translator 16 which translates the retrieved results back into the user's format, e.g. HTML. The communications services 15 then sends the results back to the user's browser 12.

The informatics management system 10 also includes drivers 17 that allow the user to operate remote application programs 19B and 19C. These remote application programs 19B and 19C may use as input parameters the results received from the data repositories 19A and 19B or alternatively, the use may provide the input parameters for the application programs 19C and 19D. The remote application programs and tools 19C may be located anywhere on the Internet or alternatively the remote application programs 19D may be located on the server 18. The gateway program 10 translates the format of the input parameters into the format required by the remote application program 19A, 19B, 19C or 19D.

The server 18 may include a data store 101 for the use and storage of retrieved data by the user. In a preferred embodiment, the informatics management system is designed so that the remote data repositories 19 and 19A and/or remote application programs 19B and 19C relate to a specific specialty or field of interest, such as biology, medicine, law, economics, etc., so that practitioners in each of such fields can use the informatics management system 10 to globally access and manage the information from the plurality of remote data repositories and use remote application programs that relate to their specialty.

II. GATEWAY AND ANALYSIS TOOL EMBODIMENT FOR MOLECULAR BIOLOGY RESEARCH

Figure 2:
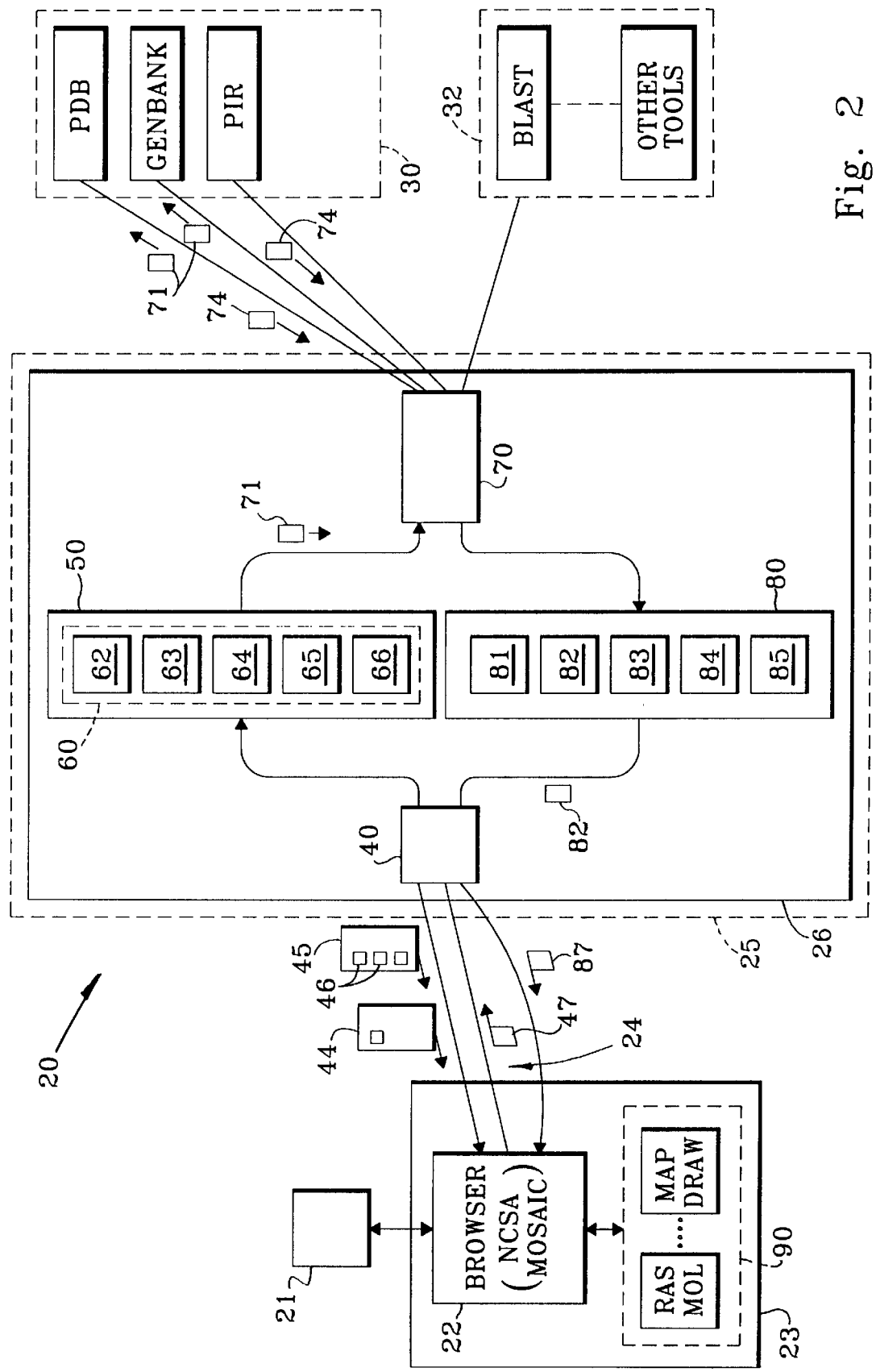
FIG. 2 is a block diagram of an embodiment of the present invention for use by biologists in accessing biology databases.

Referring to FIG. 2, in one embodiment of the present invention, there is an informatics management system 20 for use by molecular biology researchers to access and use information in various remote biological databases. The informatics management system 20 comprises a computer network gateway and set of analysis tools, as explained below.

FIG. 2 shows a general overview of the biologists' informatics management system 20. A user 21 runs client software, such as a forms-capable WWW browser 22 (e.g., Mosaic or Netscape), on a local workstation 23, such as a personal computer. The local workstation 23 connects via an http connection 24 to a server 25. The server 25 runs a gateway informatics management system 26 which includes new extensions of a set of programs referred to as "ENQUire" for "Extensible Network Query Unification System," and which also includes other programs. (In one embodiment, the server runs on a UNIX (Silicon Graphics) multiprocessor workstation, running NCSA httpd 1.4, (NCSA 1995).) The informatics management system 26 communicates with the browser 22 as a client application. The gateway program 26 interacts with the user 21 via the browser 22 and with one or more remote databases 30 and/or services 32 in a manner that permits the user to work with the remote databases 30 and/or services 32 as if they were a single entity.

In connection with this embodiment, the databases 30 and services 32 are used for biology research. In the example shown, the databases 30 include molecular and structural biology databases, such as Gen Bank, PDB, and PIR. The services 32 may include BLAST, for example.

The gateway program

The gateway informatics management program 26 includes several parts. The gateway program 26 includes a client communicating routine 40. The client communicating routine 40 sends one or more pages to the user's browser 22. The pages are forms on which the user can make selections or that include blanks into which the user can type query requests. In a present embodiment, the client communicating routine 40 sends a first page 44 to the user that permits the user to select which of the remote databases to search. The user checks all of the available databases he would like to use in the search and sends the selections back to the client communicating routine 40. Based on the selections made in the first page 44, the client communicating routine 40 sends a second page 45 to the user that permits the user to build his search request. The second page 45 includes blanks 46 into which the user can type terms to be used in searching. The user may also include boolean expressions linking the terms in the search. After the user has completed filling in the blanks 46 in the query form page 45, the user's input 47 is sent from the local workstation 16 to the server 25 where the client communicating routine 40 receives the user's query requests.

The gateway program 26 also includes a query translator routine 50 that receives the user input from the client communicating routine 40. The query translator routine 50 translates the generic user inputs into one or more different queries 71 in the specialized languages or formats appropriate for each of the one or more separate remote databases 30 or services 32 to which the queries will be sent.

The query translator 50 includes one or more translation modules 60. Typically, there would be a separate translation module (e.g. modules 62, 63, 64, 65, and 66) for each remote database or service into which the user's query is to be translated and sent. Each of the translation modules 60 translates the user's input from the generic query language used by the user into a database-specific query in one of the specific languages or formats of the remote data repositories, or an application (tool)-specific query in one of the specific languages or formats of the remote application programs (tools).

Referring again to FIG. 2, the query translator routine 50 provides its output to a database and application communicating routine 70. The database communicating routine 70 sends the translated queries 71 in parallel to the appropriate remote databases 30 and/or services 32. The remote repositories and application programs may be located anywhere in the world. The translated queries may be sent to the remote databases 30 and/or services 32 via any appropriate means, such as via the Internet or by direct telephone dial-up, or dedicated network services.

The remote databases 30 perform the requested searches and the remote application programs perform the requested analysis and calculations and send results 74 back to the server 18. The database and application communicating program 70 receives the results 74 from the databases 30 and/or services 32. The results 74 may not all be received at the same time. The database communicating routine 70 forwards the results 74 to a results translator routine 80. The results translator routine 80 collects and collates the results. The results translator routine 80 also interprets the received results back into an HTML format. Similar to the query-translator 50, the results-translator 80 may include separate modules 81, 82, 83, 84, and 85 for each of the separate remote databases and application programs (tools). The results translator routine 80 forwards the translated results 82 to the client communicating routine 40 which in turn sends the translated results 82 to the user in one or more pages 87 in HTML format. The results may be in any of several different object forms, such as sequence, graphic, plot, and table data objects.

The results may be provided to the user in a manner that permits the user to interact with the results. One mechanism for providing the user with an interactive interface is to incorporate output plots directly into the returned page by converting the plots into gif image files and adding them to the page as a clickable image using the httpd ISMAP technology. This procedure passes the coordinates of the cursor back to the http gateway, which performs actions based upon the area in which the coordinates fall. A plotting package using gd 1.2 and GD.pm is used to generate a rescalable, interactive XY plotting functionality.

The gateway program 26 is a CGI application. The gateway program 26 is composed of a set of scripts, which in a preferred embodiment are written in perl5. Two perl modules are used in the gateway program. The first is CGI.pm, which is a set of routines for generating and parsing HTML pages and forms on the fly. The second module is ACEClient, which is used to communicate with ACEDB-based genome databases. Copies of the source code of the scripts that form one embodiment of the gateway program 26 are included in the appendix of this specification. Use of perl5 provides a number of advantages, including string intrinsics, object-oriented programming, and the interpretive nature of the language which allows for the dynamic addition of translation modules without the need for recompilation. Perl is relatively platform independent, allowing the gateway program 26 to be installed on different UNIX systems without recompilation.

Figure 3:
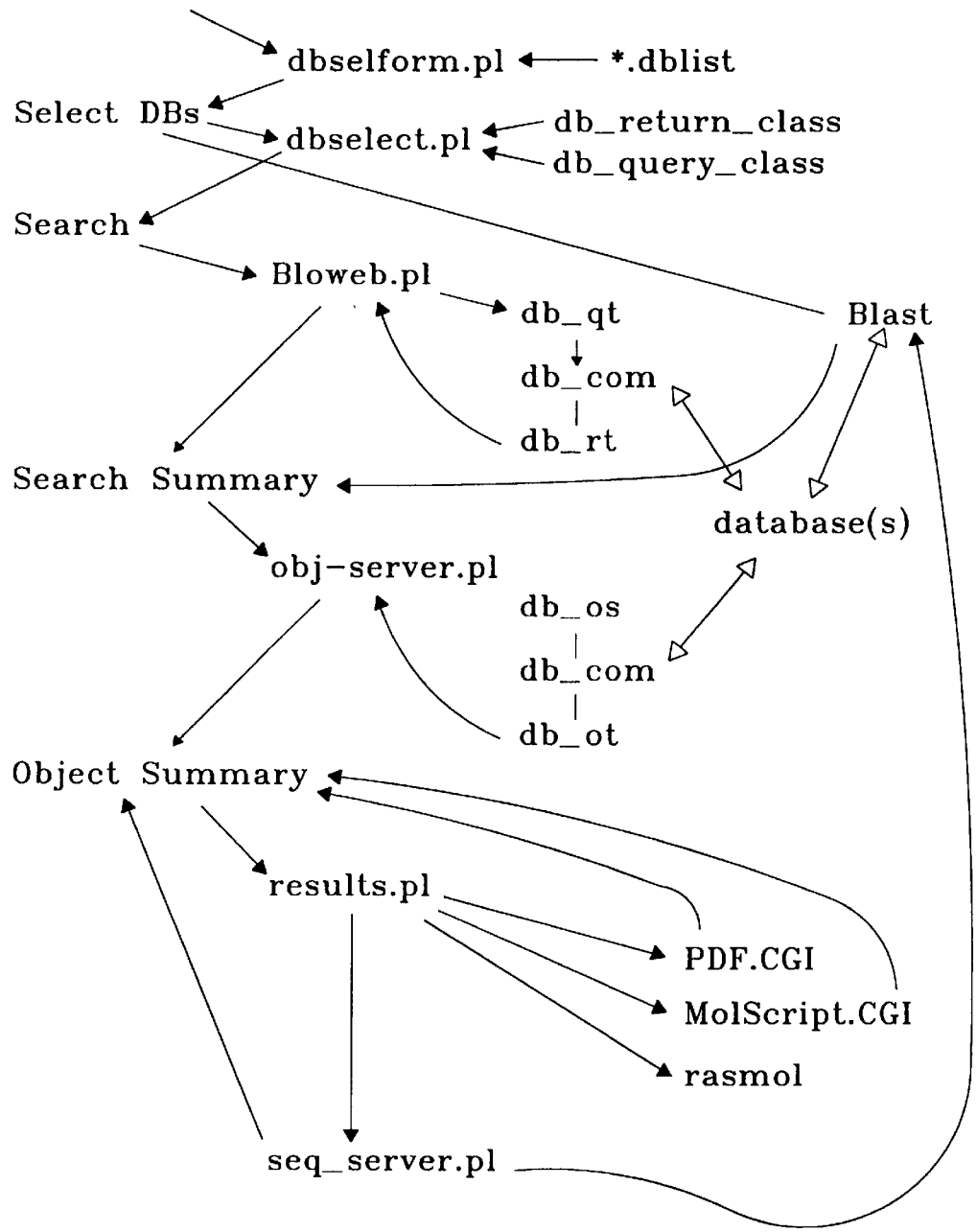
FIG. 3 is a diagram illustrating program flow and data flow among the scripts that comprise the gateway program of FIG. 2.

FIG. 3 shows the communication paths and perl programs linked together to form an embodiment of the gateway program 26. On the left side of FIG. 3 are the screens that are presented to the user on the user's workstation. On the right side of FIG. 3 are the remote resources (databases 30 and services 32). In the center of FIG. 3 are the scripts that connect them together. Solid arrows indicate program control flow, while open double ended arrows indicate information transfer. Since the program results are treated as either search or object summaries, the user does not have to leave the browser environment to interact with the results.

ACeDB and SolGenes are organism specific genome databases. ACeDB contains information about the nematode *C. elegans*, while SolGenes contains information about the genus Solanaceae (potatoes, tomatoes, and peppers). The databases are queried using the perl module Aceclient.pm, accessing the aceserver maintained at the National Agriculture Library, and results are formatted into HTML using the perl module AceWWW.pm.

Entrez federates several biological sequence databases and a literature reference database. The sequence portion of Entrez contains sequences of multiple organisms from Genbank, EMBL, Swiss-Prot, while the references portion consists of the molecular sequence data subset of Medline. Entrez is accessed using nclever, a command line interface to the network Entrez server.

PDB (Brookhaven Protein Data Bank) is the repository for protein structures from crystallography and NMR studies. For purposes of the workbench, the PDB installation has been mirrored at NCSA, and has been extracted into index files which are searched by custom search routines.

PIR (Protein Information Resource) is a collection of macromolecular sequences. PIR is accessed via the NBRF program ATLAS.

The WBG archive is a full-text and figures hypertext version of the *Worm Breeder's Gazette*, and informal newsletter for *C. elegans* researchers published by the Caenorhabditis Genetics Center. The articles are stored at NCSA and are indexed and searched via a Glimpse server.

Several of these data sources do not support complex queries. The ACEDB-based databases and PIR support operations upon a single keyset. To allow the user to create complex queries involving boolean operations on multiple sets, each atom (i.e., each target-field-term combination) can be queried separately, and the results are combined logically by the results translator.

The helper applications

Examples of remote applications include, but are not limited to NCBI BLAST, SSEARCH, MSA, CLUSTALW, SIM, ALIGN, AMPS, AMAS, LALIGN, STAMP, fastDNAML, PHYLIP, ClustalW, Boxshade, VisProt, ALSCRIPT, Modeller, ProfileScan, PDF, DSSP, LIGPLOT, HBPLUS, PROCHECK, VOLBL, ALVIS, Sleuth, ASC, TMpred, TMAP, GARNIER, CHOFAS, HTH, PHD, PSSP, nnPredict, ZIPSCAN, and Kinsim/Fitsim.

Figure 4:
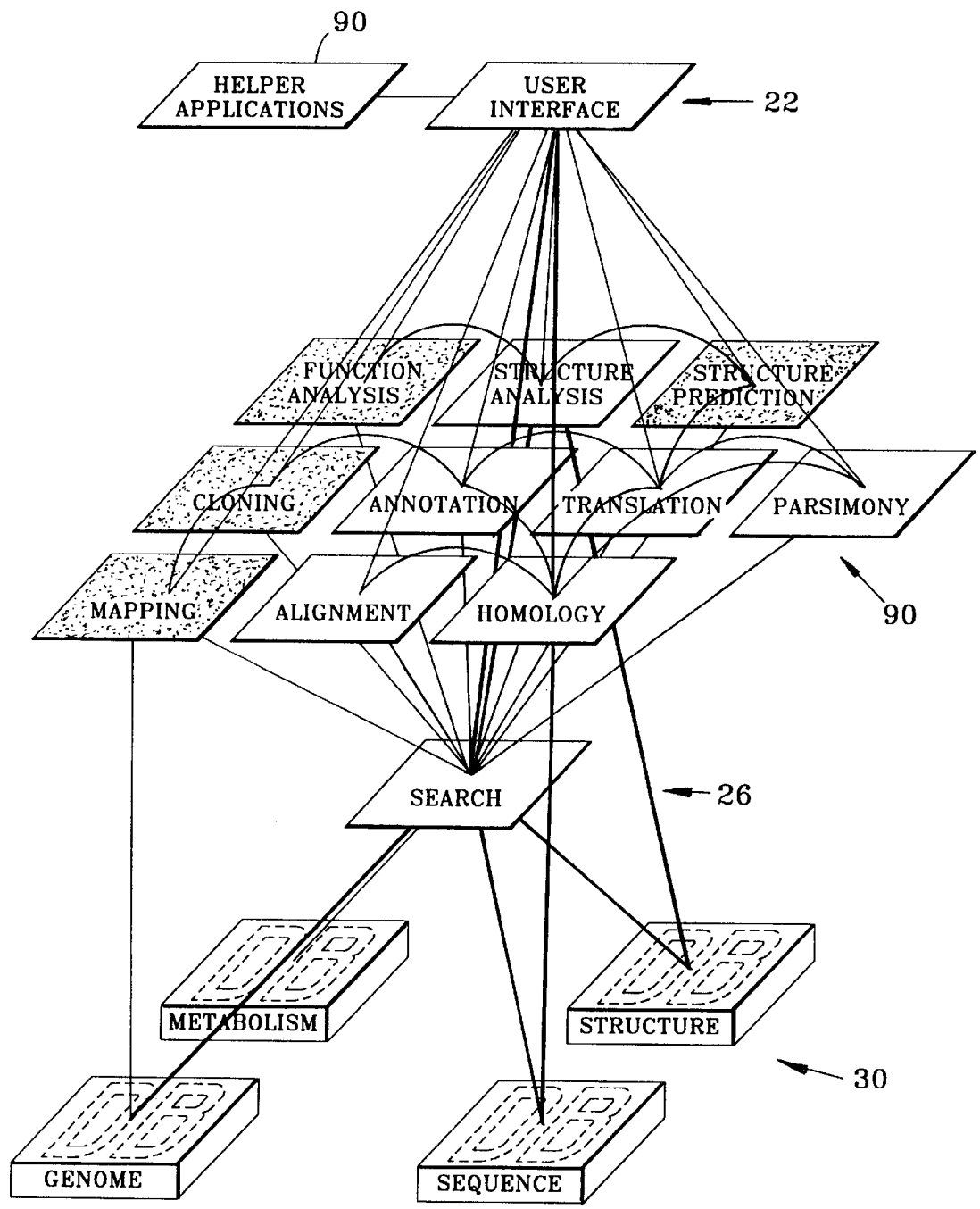
FIG. 4 is a diagram illustrating the interrelationships between the interface, tools, gateway, and remote data repositories in the embodiment of FIG. 2.

FIG. 4 shows a schematic view of how different subcategories of tools and helper applications interact with the client application 22 and with the databases 30 and with other categories of tools 32 helper applications 90. The helper applications 90 may be located on the user's workstation 23. The tools 32 may be located on the server 25, or on remote systems.

Some of these helper applications 90 provide support for information formats that may not be supported by the user's browser application 22, for example, the molecular visualization program RasMol. These helper applications include conventional analysis tools that are already available in the public domain and that are used by many researchers. These tools and helper applications include RasMol, XV, ACE/gr, and Ghost view.

One tool that can be used, PDF, is a protein analysis algorithm that constructs atom-pair distance probability density functions from unique high resolution protein structures and uses them to assess, refine and predict protein structures. PDF is too compute-intensive to run on most client workstations. It will typically run on the server, or perhaps a remote supercomputer.

The tools may also include tools that are available commercially. With respect to commercially available tools, the gateway program provides export functions so that researchers who have such commercially-acquired tools can link them into the system as helper applications.

The informatics management system 20 also includes instructions and reference material for the tools and databases. The reference material includes an interface page for each tool that contains links from a short description of the option selections to pages that explain the options in detail. The short descriptions provide the user with on-line help reminders about the functions and effects of each option. The pages with the detailed descriptions provide a detailed explanation of the tool programs and algorithms used. This second layer of documentation enables biologists to decide which tool is best suited to the task at hand, improving the quality of computational analysis in the community.

METHODS OF OPERATION

EXAMPLE 1

Three screens presented to a user in a sample query session are shown in FIGS. 5A, 5B, and 5C. The three screens show what would be displayed by the browser, representing (in FIGS. 5A, 5B, and 5C) the three steps in making a query. The screen in FIG. 5A is the database selection screen. This screen is an example of the "page 44", described above and shown in FIG. 2. The database selection screen includes check boxes that can be selected that allow the user to choose which databases to search. An appropriate federation of the databases' return types and query types are computed, and a query-builder form is returned to the user (FIG. 5B). The screen in FIG. 5B is an example corresponding to the second "page 45", described above. The user can build a complex query of up to seven terms, nested by parentheses and linked by either AND or OR. In this example the user specified two sequence databases, PIR and PDB. The screen in FIG. 5A shows the initial database selection possibilities, as presented to the user. The screen in FIG. 5B shows the query builder screen, which permits the user to do a federated search for particular kinds of objects in two or more databases simultaneously. In this example, the user searched for all proteins relevant to the identifier, "secretory trypsin inhibitor". The screen in FIG. 5C shows the results of the search, with a scrollable window, "Collective Results", which shows all objects that were found from both databases during the search. The screen in FIG. 5C is an example corresponding to the results screen "page 87" of FIG. 2.

The query federation process illustrated in FIGS. 5A, 5B, and 5C is at the syntactic (field names) level. Basic biological types are given common names, and the common names are translated into the proper terminology for a specific database. The search engine translates the idiom of particular databases into a federated query language. For example, the objects searched for in the example of FIGS. 5A–5C are designated "sequences" in the idiom of the PIR database and "compounds" in the idiom of the PDB database. Because the sequences listed in the PIR database are the amino acid sequences that define proteins, and because the compounds in the PDB database are proteins, the search engine translates the fields "compounds" (PDB) and "sequences" (PIR) into the common identifier "proteins" for purposes of the federated search shown in FIGS. 5A–5C.

Figure 6:
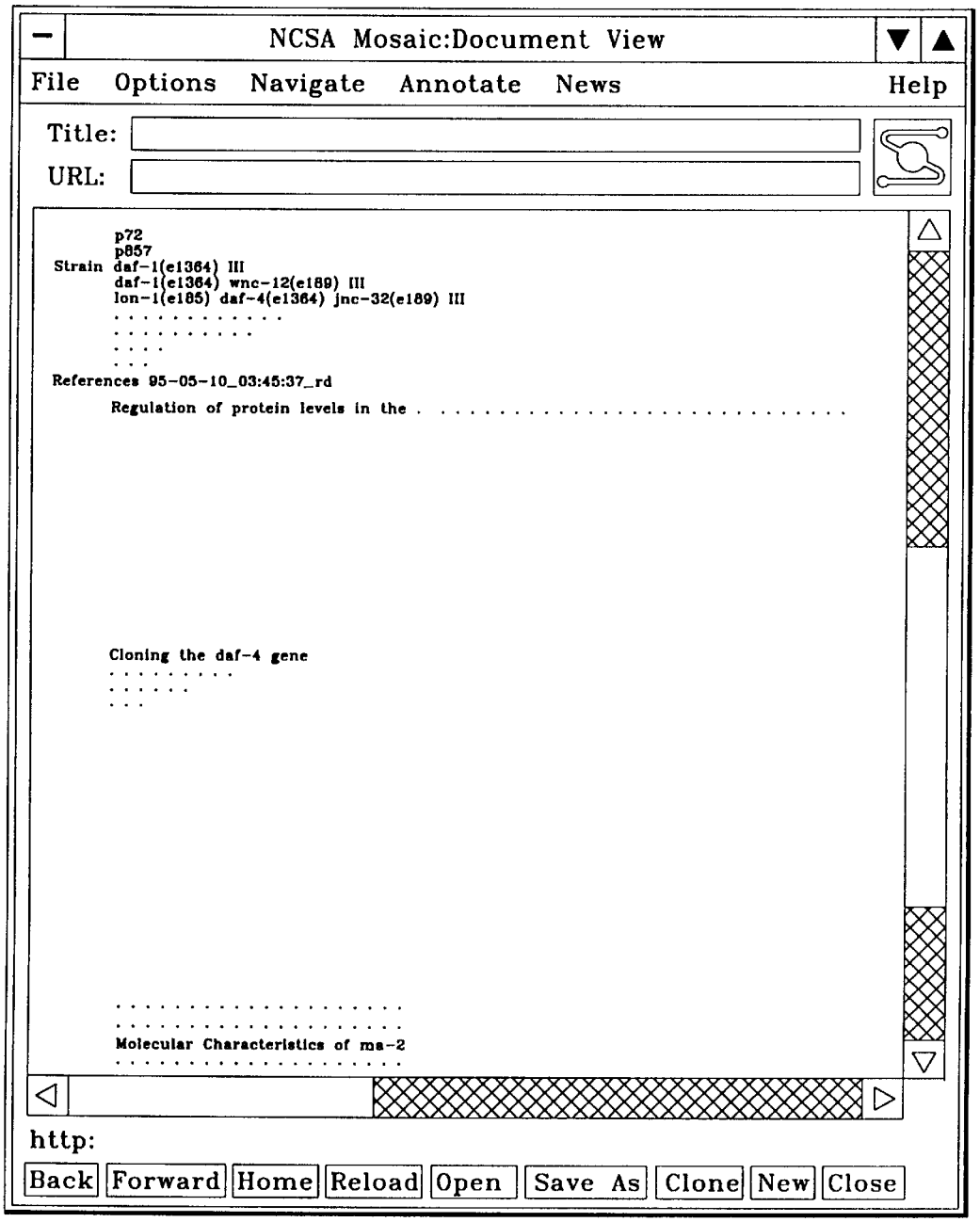
FIG. 6 is an illustration of another results screen in another exemplary use of the embodiment of FIG. 2.
Figure 7:
FIG. 7 is an illustration of a results screen in another exemplary use of the embodiment of FIG. 2 where a redirection has occurred so that an HTML page from the WBG archives at NCSA was retrieved, as opposed to the normal ACeDB object for the same item, shown in FIG. 8.

Following links from the results summary will connect the user with pages drawn from the original databases. Examples of such results pages are shown in FIGS. 6 and 7. In FIG. 6, the daf-4 gene entry from ACeDB has been retrieved from the WWW ACeDB server at USDA/NAL and scrolled down to view the references. The ACeDB server delivers a perl5 object, which is translated into HTML with the links pointing at the search engine object server script. Each link (underlined text on the displayed page) in the entry points at an object server specific for that database, which creates the proper query to retrieve and translate objects from that database. The object server can redirect requests, retrieving an object from a more canonical source, creating a semantic (field value) level federation.

Figure 8:
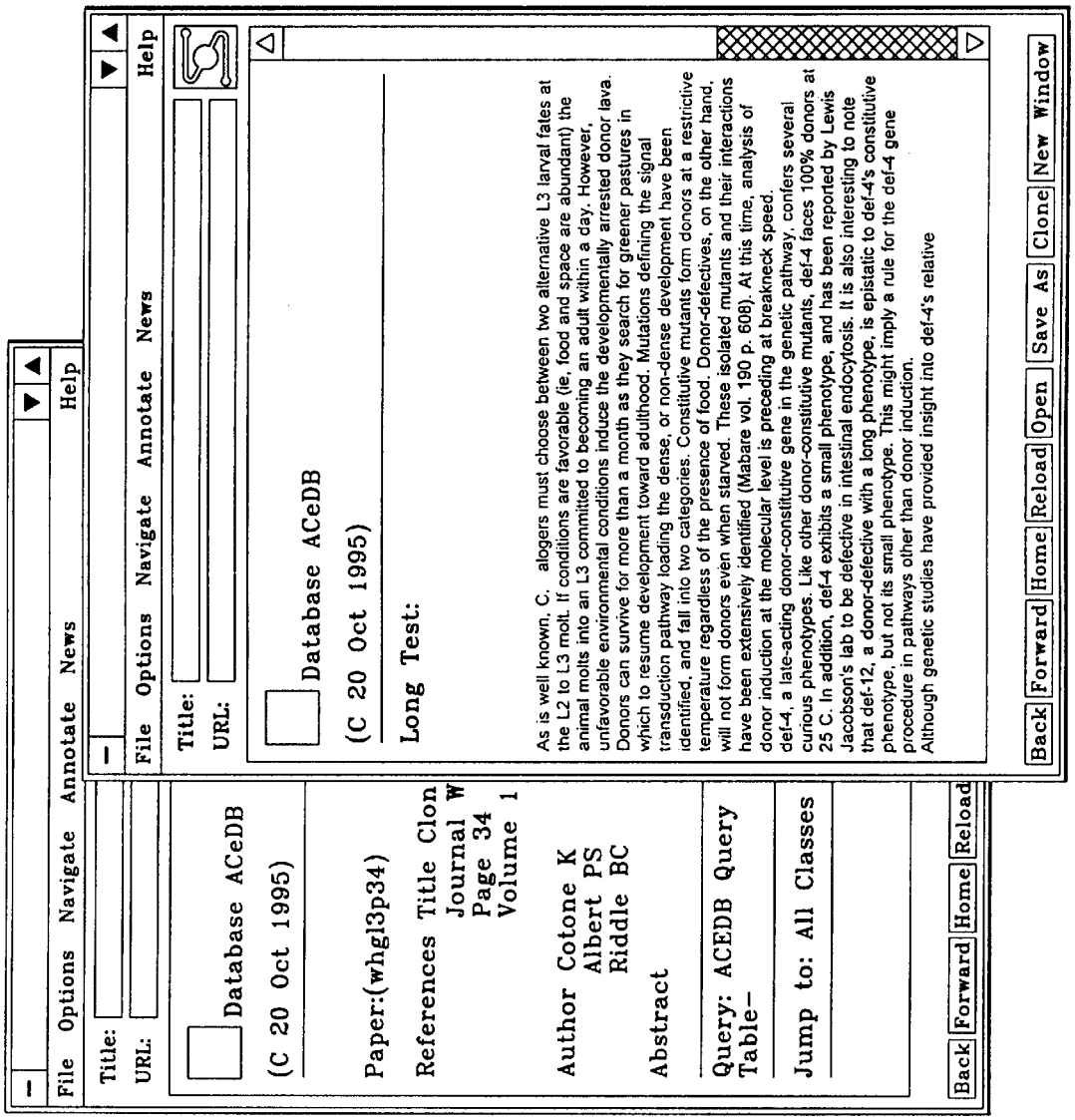
FIG. 8 is an illustration of the same results as shown in FIG. 7, except that the results were retrieved from the ACeDB database and are not hypertext linked.

FIG. 7 shows the result of retrieving a *Worm Breeder's Gazette* article from the ACeDB object server. A redirection has occurred, and the HTML page from the WBG archives at NCSA has been retrieved, as opposed to the normal ACeDB object for the same item, shown in FIG. 8. The ACeDB version of the text is not hyperlinked, and is presented as a database record rather than as a document. The internal links in the hypertext document point at the ACeDB object server, since all the links refer to *C. elegans* genes. The WBG documents in the NCSA archive provide an enhanced presentation of the data. The same semantic federation can be used to follow sequence accession numbers between literature and sequence databases. The net result of redirecting the fetches is an apparent increase in the dataspace seen by the user.

EXAMPLE 2

As mentioned above and pictured in FIGS. 5A–5C, the gateway program can merge the results from different databases thus presenting the user with a list of objects and potential databases from which to retrieve them, rather than a list of databases and the objects found within. In addition, this further embodiment would allow the user to select multiple database objects, load them into his workspace, and then submit the object to various tools. FIGS. 9A and 9B show this further function.

In the screen of FIG. 9A, the user has loaded into the workbench four objects (in this case database entries for particular proteins) from the list that was collected in FIG. 5C. Then the user entered these objects as data into a program for multiple sequence alignment, which returned the output shown on the screen in FIG. 9B.

EXAMPLE 3

As mentioned above, the informatics management system can be augmented by tools or helper applications 90 on the client workstation. Helper applications may be spawned by the user's web browser on demand. The helper applications may be used to either display data that the browser is incapable of displaying, or to place data within a secondary application for manipulation. When a file is transmitted to the browser, the file header is read for information about the content type. If an unfamiliar content type is found, the browser consults external MIME files for the type and the application to be used. The proper application is launched, and the file is loaded into the application.

Figure 10:
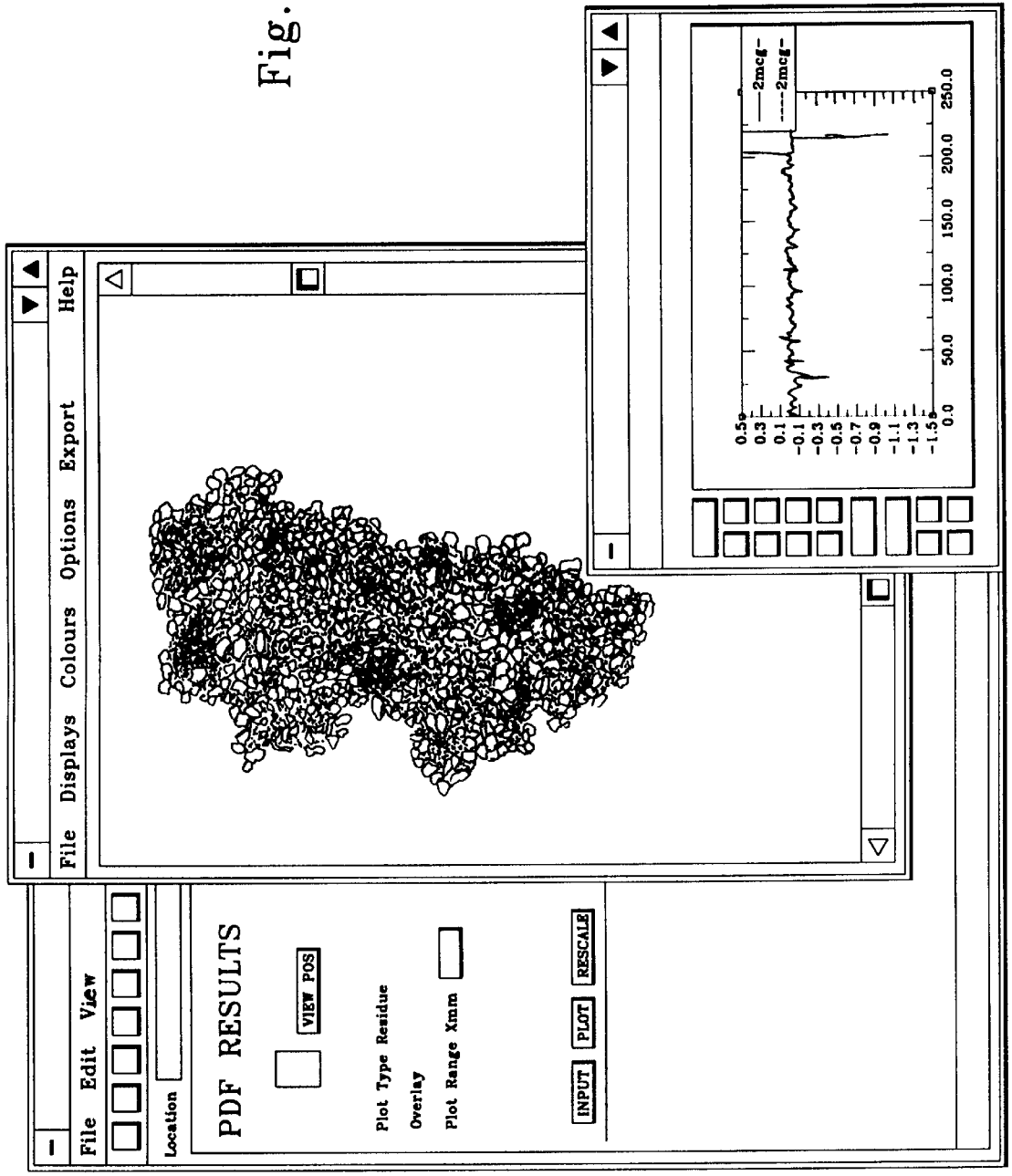
FIG. 10 is an illustration showing screens presented to a user during an exemplary operation of the embodiment of FIG. 2 including an additional results screen in which a helper application has been run on the results.

An example using the macromolecular viewer RasMol as an external viewer for PDB files is shown in FIG. 10. A probability distribution function profile was calculated for the IgG Benze-Jones molecule, and the results viewed by having the browser launch a RasMol window with the PDF file. The resulting image can now be rotated and viewed or color coded according to improbable regions of the structure, using the RasMol program running on the local machine. Additional information is seen in the plot window, which was launched by the same mechanism.

EXAMPLE 4

Figure 11:
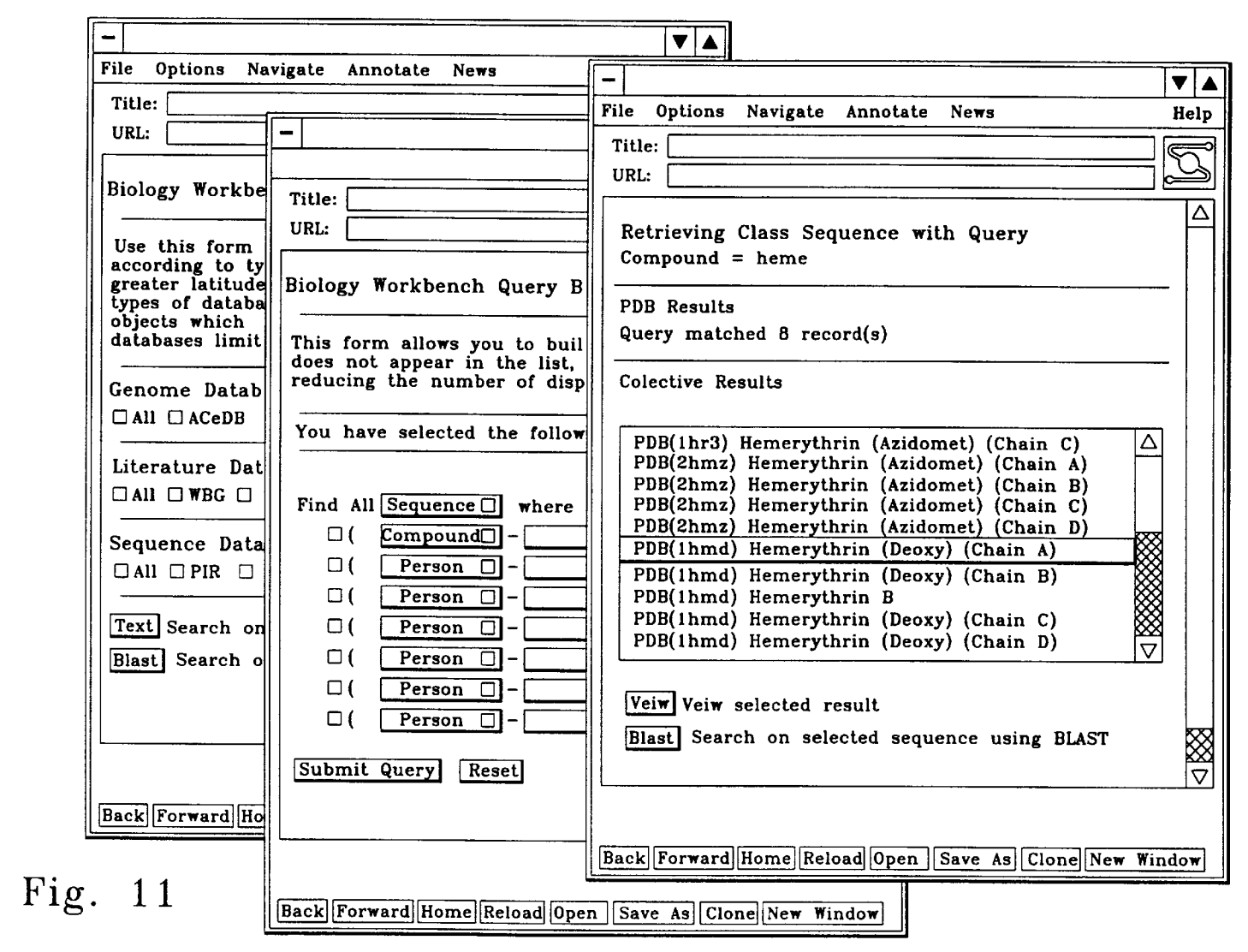

In FIG. 11, an initial screen (left) is presented on the user's workstation via the browser application. This screen is one of the query pages 44 described above. The screen on the left of FIG. 11 allows the user to select one or more of the databases 30 and then to search them using either a text search or a BLAST search. The search illustrated in FIG. 11 is a text search, with the query being built in the center screen (corresponding to the second query page 45) and the integrated results are shown in the right screen. The right screen is one of the results pages 87 sent by the gateway program 26 to the user's workstation. The user can then select a result and view it, or submit it to other analysis programs, such as one of the tools 32.

EXAMPLE 5

Figure 12:
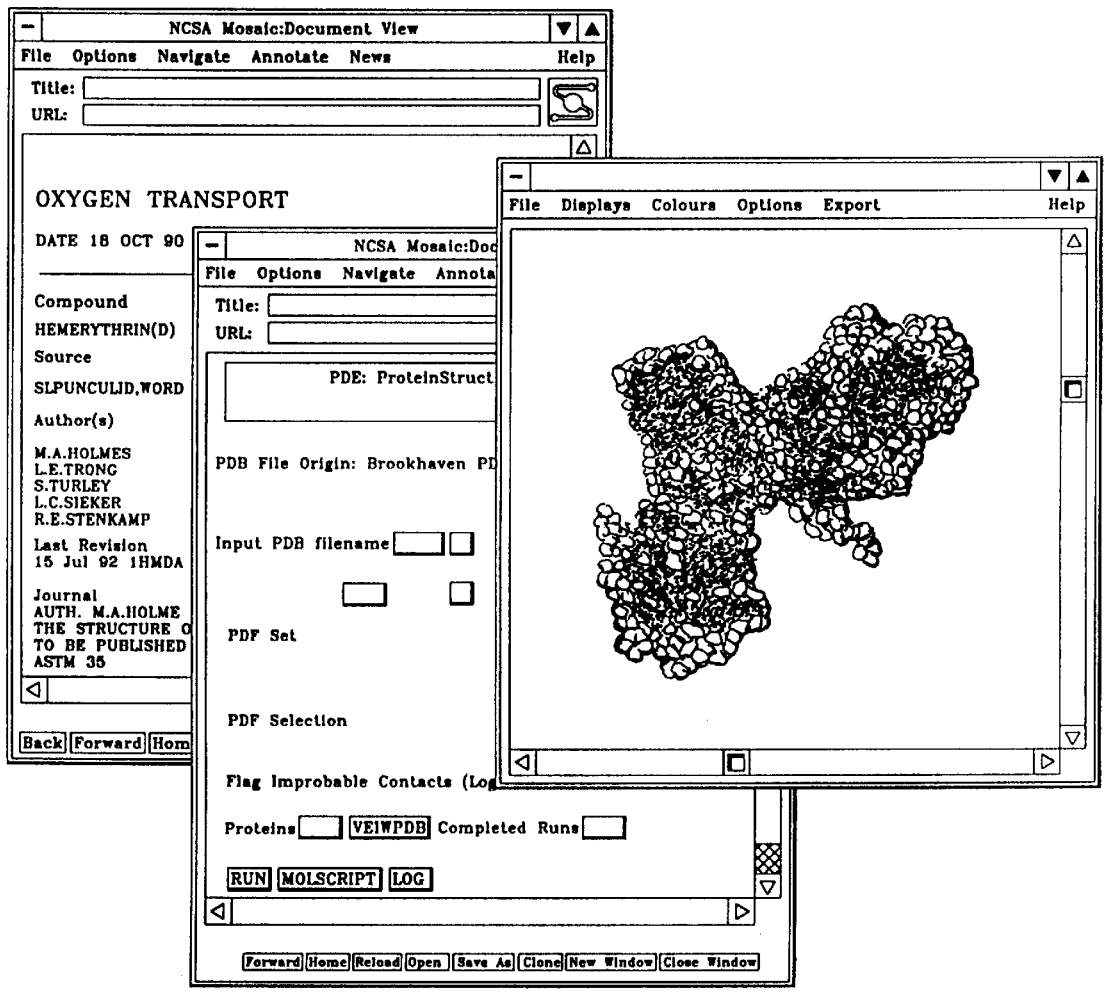
FIG. 12 is an illustration showing screens presented to a user during another exemplary operation of the embodiment of FIG. 2 including a results screen in which a helper application has been run on the results.

Another example is shown in FIG. 12. FIG. 12 shows three screens, in which a PDB file has been selected (left screen) and viewed, and then submitted to the PDF program (center screen), which computes the accuracy of the protein structure based upon a distance probability distribution function. The output is viewed using the helper application RasMol (right screen). The PDF program, which requires several minutes to run on a supercomputer, is made accessible to all users (even those on PC's) by the biologists' informatics management system 26 (FIG. 2).

Advantages of the present embodiment

The informatics management system 20 (reference FIG. 1), including in particular the gateway program and set of drivers for analysis tools and translators for databases, provides a seamless, WWW-based user interface with static, spawned, and dynamic components, accessible to any researcher-user with a computer connected to the Internet. The informatics management system provides links to major molecular biology databases or other databases that have information relevant to biology research. The informatics management system provides a dynamic database manager that integrates the many existing databases without duplicating them. A significant advantage of the informatics management system 20 is that a user can use a standard browser interface to access multiple databases and see the results without the potential loss of nuances.

A single query can gather results back to the user from multiple remote data repositories. Since the queries are done in parallel, there is a great time savings when querying multiple databases.

Further alternative embodiments

1. In a further embodiment of the system, there are provided helper applications that use computing resources that may reside on the server 18 or may be located at a site remote from both the user's workstation 23 and the server 18 (see, FIG. 1). Such remote computational resources may include supercomputing resources (as described in Example 5, above). For example, Message-Passing Interface (MPI) implementations of compute-intensive algorithms provide fast response to users, and efficiently utilize national shared memory processors (SMP) architectures. Web-based access to such supercomputers may be provided by means of a driver 17 (FIG. 1) on the server 18 that communicates with the remote super/computing resource. This is especially advantageous in the analysis and parsing of genome sequences, in building additional tools for genetics, cloning, and molecular biology, in enhancing tools for sequence-structure analysis, in homology modeling, in crystallography and NMR modeling and refinement, and in sequence-structure-function tools.

2. Additional remote biological databases can be readily added. Adding new databases requires only that some method of remote access exist. Possible additional biology databases include the Swiss-PROT and EMBL sequence databases, more genome databases like GDB and Flybase, as well as the myriad of small genomes that are based on ACEDB. Incorporation of the latter is simplified by the ACeDB translator which can be used as a template to incorporate others. Other classes of databases, such as enzyme and metabolism databases, may also be added. Additions of new databases may require additional database translators (i.e. query translator modules 60 and results translator modules 80). The databases do not need to be mirrored in any way, although some of them may be mirrored locally for more rapid access.

3. Existing WWW technology is stateless providing for only inquiry-response interchange. No record of the state of the inquiry is typically saved by the server. However, a stateful system can be emulated by passing hidden variables back and forth between the client and the server, thereby making the HTML form into a "state" repository. Thus, in a further alternative embodiment of the informatics management system, the gateway program includes a routine by which a unique user identifier is passed between the browser client and the workbench. Information about the state of the user's query or computation is stored on the server side, and accessed by the server as needed. This reduces the document size and saves transmission time in subsequent communications.

4. Referring again to FIG. 1, in a further embodiment of the informatics management system, the user is provided with a workspace 101 on the server 18. Addition of a user workspace (also referred to as a "data store") is facilitated by the use of unique identifiers and session control, mentioned above. The data store represents a temporary storage area in which the user can create unique databases from subsections of other databases. For example, a biologist researcher user might want to create a sub-database of only sequences from GenBank and PIR which have kinase domains, then search that using the BLAST algorithm.

5. In present embodiments, the code for the helper applications is resident (and executable) on the user's workstation or on the server. In an alternative embodiment, helper application may be downloaded to run within the browser. A HotJAVA browser from SunSystems is an example of a browser with this capability. Scripts written in JAVA can be sent to the user's browser and executed there, allowing interactive viewers to remain within the web browser and alleviating the need to install special viewers and applications for each program.

III. Medical Informatics Management System

In the above embodiment, an informatics management system was disclosed that was suitable for managing informatics for biologists, and in particular, for managing the collection of information from a myriad of diverse data repository systems used by molecular biologists. There are numerous other specialty fields that are served by myriads of information repository systems. Alternative embodiments of the present invention can be constructed for such other specialty fields as well. Such alternative embodiments are regarded as within the scope of the present invention.

Figure 13:
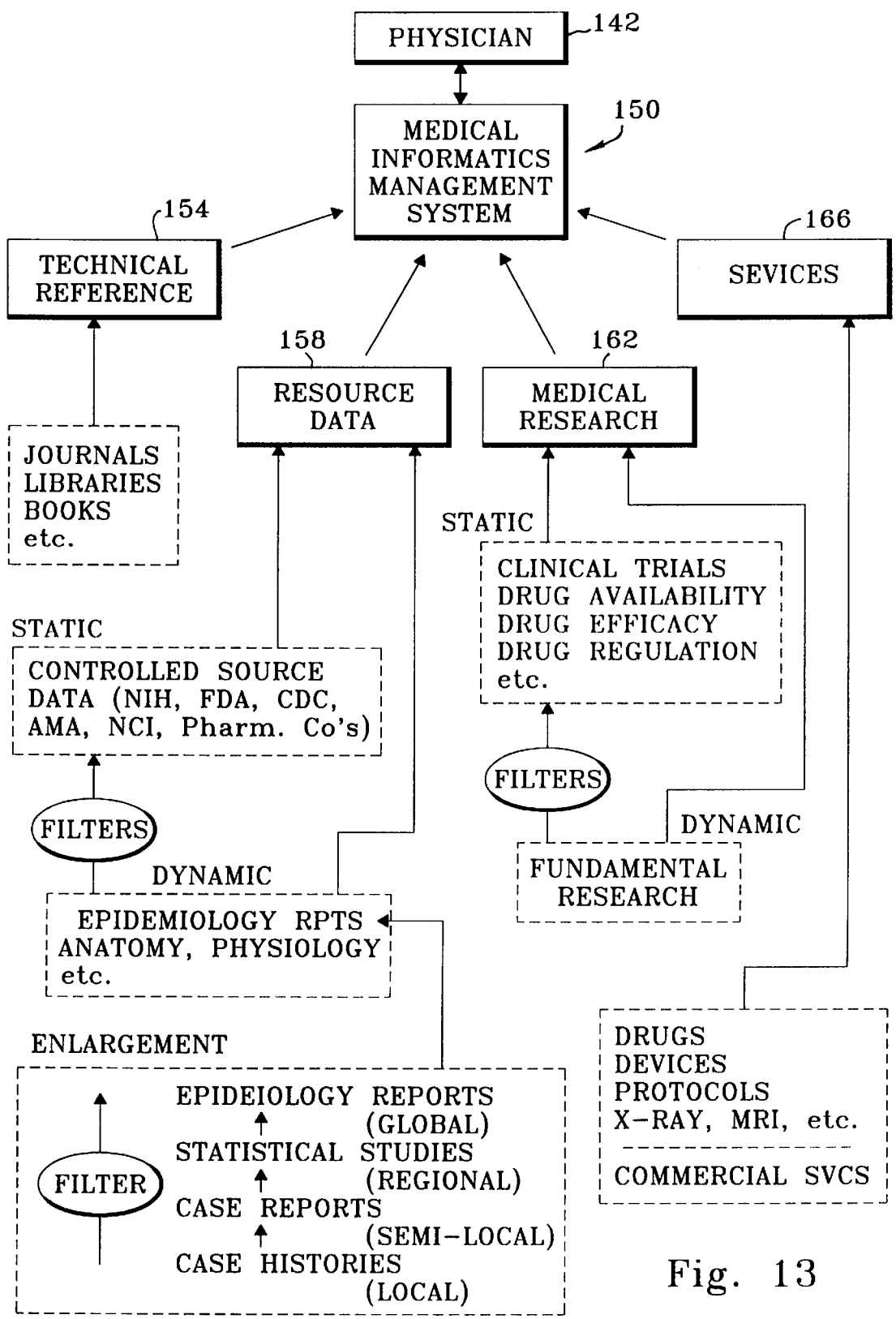
FIG. 13 is a block diagram of an embodiment of the present invention for use by the medical community.

One field that is well-suited to be served by an informatics management system is the field of medicine. A block diagram of an embodiment of an informatics management system 150 for the field of medicine is shown in FIG. 13. The medical informatics management system 150 would include some of the same components as the informatics management system used for biology research, described above.

Figure 14:
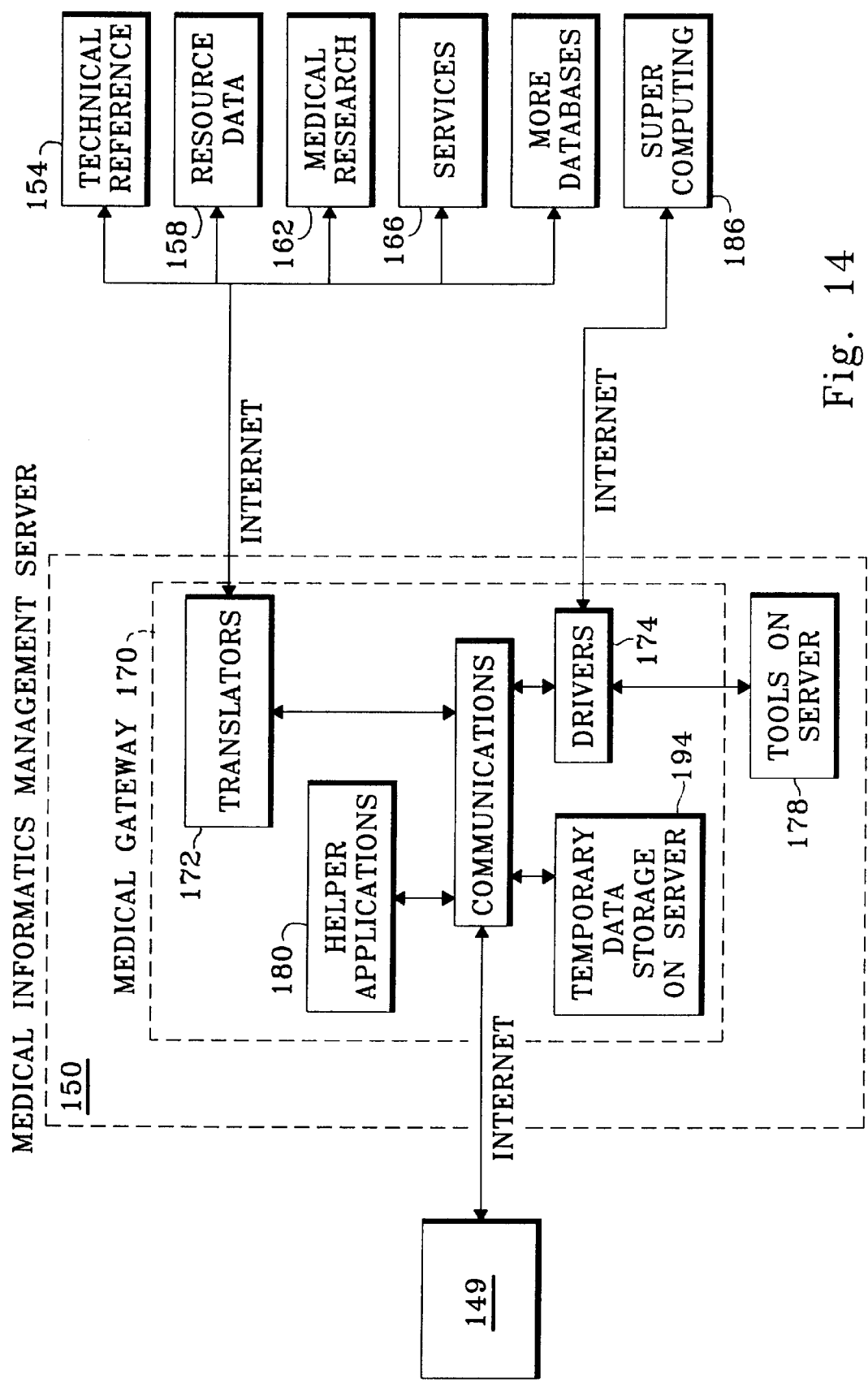
FIG. 14 is a block diagram showing the embodiment of the informatics management system of FIG. 13.

Referring to FIG. 14, the users 149 of the medical informatics management system 150 would include physicians that provide patient care and treatment, as well as other members of the medical community, such as medical researchers, medical staff and technicians, medical service providers, insurance companies, and so on.

The medical informatics management system 150 would access remote data repositories related to the field of medicine. These remote data repositories would include technical reference repositories 154, resource data 158, medical research and technical discipline data storage systems 162, and service provider data storage systems 166, among others.

The technical references repositories 154 would include libraries, and publishers of journals and books, who would make their publications available to physicians and other users of the medical informatics management system 150.

The resource data providers 158 would include providers of controlled-source data, such as NIH, FDA, CDC, AMA, NCI, ACP, pharmaceutical companies, etc., to easily make available such static data as epidemiology reports and drug product outlines. Dynamic data, even down to case histories, would be available if the physician-user requests such data and if the owner of the data chooses to make the information available.

The medical research databases and technology application disciplines 162 (e.g., anatomy and physiology) would include institutions and groups whose primary missions require access to a broad range of information in situations where the information required cannot be fully specified a priori. The medical informatics management system 150 offers these groups an effective way to provide the rest of the medical community with both static information (e.g., clinical trials, drug availability, drug efficacy, drug regulation) and dynamic leading edge knowledge in such fast moving fields as molecular medicine.

The medical informatics management system 150 offers service providers 166 the same access to physicians (and vice versa) as is offered to all information providers. This includes not only support services such as record keeping, but also direct-benefit medical services such as X-ray, MRI, protocols, drugs, and devices.

Referring to FIG. 14, the medical informatics management server 150 would include the same Web-based, client-server architecture as the biologists' system 10 (see, FIG. 1). The medical system 150 includes a gateway program 170. The gateway program 170 would include components similar to the gateway program of the biologists' system and would perform essentially similar functions. The medical gateway program 170 would include appropriate translators 172 and program drivers 174 for accessing the remote data repositories 154, 158, 162, 166, and so on. The translation libraries 172 would be suited for the remote medical databases or systems to be accessed. As in the system used for biology research, the medical gateway program 170 is easily expandable allowing for modular development and functional growth.

In addition to the gateway program 170, the medical informatics management server 150 would also include appropriate tools 178 or helper applications 180 that would operate on the retrieved data to provide enhanced functionality for the user. Some of the tools would be similar to the tools used in the biologists, informatics system, however, other tools would be different in order to work with the different types of data in the medical informatics management system. These tools 180 would provide technical features to support the needs of the medical community. In the case of applications requiring very large memory or computing cycles, the job may be farmed out to a super-computing center 186 directly through the Web-page interface. The medical informatics management system 150 may also include a user data store or disk space 194, similar to the embodiment for biologists.

The medical informatics management system 150 enables medical practitioners, and other users in the medical community, to access and use multiple remote databases and services as if they were a single entity. The medical informatics management system 150 permits the medical user to interact simultaneously with different repositories of information distributed across the Internet, and to do whatever computations are permitted by those repositories upon repository information, using that information. This is accomplished without transmitting any more data than is ultimately desired by the requesting medical-user. Control of and access to information remains with the information owners.

IV. Other Alternative Embodiments

Informatics management systems, similar to those described above for biologists and the medical community, may be tailored for other fields or specialties, such as law, economics, government, etc. Not all remote data repositories associated with these various fields or specialties are organized as those discussed above, and accordingly, the translators and drivers for informatics management systems for any of these fields or specialties would be tailored to work with the format of each particular data repository. However, the gateway program portion of the informatics management system for any of these other specialties would be essentially similar.

It is intended that the foregoing detailed description be regarded as illustrative rather than limiting and that it is understood that the following claims including all equivalents are intended to define the scope of the invention.

We claim:

1. A method of managing informatics in a networked system comprising:

from a client workstation on the networked system, sending a query request to a server on the networked system to search for information, said query request being in a first format;

from the server, receiving the query request from the client workstation and translating the query request into a plurality of translated query requests in different formats;

from the server, sending the plurality of translated query requests in different formats to a plurality of remote data repositories;

on the server, receiving a plurality of results from the plurality of remote data repositories to which said plurality of translated query requests were sent;

on the server, translating the plurality of results into results in the first format; and from the server, sending the translated results in the first format to the client workstation.

2. The method of claim 1 wherein said step of translating the received results into the first format further comprises the step of formatting the results into HTML.

3. The method of claim 1 further comprising:

using software tools to manipulate the translated results, said software tools located on said client workstation.

4. The method of claim 3 wherein said software tools are launched from a browser application running on said client workstation.

5. A method of managing informatics and doing computing in a networked system comprising:

from a client workstation on the networked system, sending a query request to a server on the networked system to execute at least one search for information, said query request being in a first format;

from the server, receiving the query request from the client workstation and translating the query request into a plurality of translated query requests in different formats;

from the server, sending the plurality of translated query requests in different formats to a plurality of remote data repositories;

on the server, receiving a plurality of results from the plurality of remote data repositories to which said plurality of translated query requests were sent;

on the server, translating the plurality of results into results in the first format;

from the client workstation on the networked system, sending a command to the server to execute at least one remote application, utilizing as input to the remote application program the translated results in the first format;

on the server, receiving the command from the client workstation and sending the translated results to the remote application;

on the server, receiving application results from the remote application; and from the server, sending the application results to the client workstation in the first format.

6. The method of claim 5 further comprising the step of:

on the server, after the step of receiving the command from the client workstation, translating the command into a format other than the first format; and wherein the command is sent to the remote application in the other-than-first format.

7. The method of claim 5 further comprising the step of:

on the server, after receiving the application results from the remote application, translating the application results into the first format.

8. The method of claim 5 further comprising the step of:

prior to the step of sending a command from the client workstation, sending a second message from the server to the client workstation requesting input for formulating an execution command for at least one remote application program.

9. The method of claim 8 wherein the second message comprises at least one page requesting selection of which remote application program to execute and parameters for execution of the selected remote application program.

10. The method of claim 9 wherein the selection of which application is on a first page and the selection of parameters for the application program are on a second page.

11. The method of claim 5 wherein at least a portion of the application results are kept in a data store on said server.

12. The method of claims 1 or 5 further comprising the step of:

prior to the step of sending a query request from the client workstation to the server, sending an initial message from the server to the client workstation, said initial message requesting input for formulating a search of said remote data repositories.

13. The method of claim 12 wherein said initial message comprises at least one page in HTML format.

14. The method of claim 12 wherein said initial message comprises a first page requesting selection of which remote data repositories to search and a second page requesting terms to be searched in the selected remote data repositories.

15. The method of claim 12 wherein said initial message requests selection of which remote data repositories to search and which terms to be searched in the selected remote data repositories.

16. The method of claims 1 or 5 wherein said query request is sent from a forms-capable browser application running on said client workstation.

17. The method of claims 1 or 5 wherein said networked system includes the Internet.

18. The method of claims 1 or 5 wherein said server and said client application are connected to the Internet.

19. The method of claims 1 or 5 wherein said remote data repositories are accessible via the Internet.

20. The method of claims 1 or 5 wherein said step of sending the plurality of translated query requests to the remote data repositories is done in parallel.

21. The method of claims 1 or 5 wherein said query request is sent from a browser application running on said client workstation and wherein said results in the first format are sent from said server to said browser application.

22. The method of claims 1 or 5 further comprising the step of:
    inserting hypertext links into the results before sending the results to the client workstation.

23. The method of claim 22 wherein the inserted hypertext links point to additional pages from the data repositories.

24. The method of claims 1 or 5 wherein said remote data repositories include biology information.

25. The method of claims 1 or 5 wherein said remote data repositories include at least one of the following databases: ACeDB, SolGenes, Entrez, PIR, and the WBG.

26. The method of claims 1 or 5 wherein the remote data repositories are genome databases.

27. The method of claims 1 or 5 further comprising:
    maintaining a data store on said server for a user of said client workstation.

28. The method of claim 27 wherein at least a portion of said plurality of results from the plurality of remote data repositories are kept in said data store.

29. A method of managing informatics and doing computing on a system connected to the World Wide Web including a means for building a command for a remote program, the method comprising:
    sending a first Web page over the Internet to a client's browser, said first Web page including a means for building a command for executing a remote program;
    receiving an execution command over the Internet from the client's browser in response to the first Web page, said execution command being in a first format;
    translating the query into a second format;
    sending the execution command in the second format over the Internet to at least one remote application program;
    receiving results over the Internet from the remote application program;
    translating the results received from the remote application program into results in the first format; and
    sending the results in the first format over the Internet to the client's browser.

30. The method of claims 5 or 29 wherein said remote application program includes at least one of: NCBI BLAST, SSEARCH, MSA, CLUSTALW, SIM, ALIGN, AMPS, AMAS, LALIGN, STAMP, fastDNAML, PHYLIP, ClustalW, Boxshade, VisProt, ALSCRIPT, Modeller, ProfileScan, PDF, DSSP, LIGPLOT, HBPLUS, PROCHECK, VOLBL, ALVIS, Sleuth, ASC, TMpred, TMAP, GARNIER, CHOFAS, HTH, PHD, PSSP, nnPredict, ZIPSCAN, and Kinsim/Fitsim.

31. The method of claims 5 or 29 wherein said remote application program provides for the analysis of biological information.

32. A method of managing informatics on a system connected to the World Wide Web, comprising:
    sending a first Web page over the Internet to a client's browser, said first Web page including a means for building a query;
    receiving a query over the Internet from the client's browser in response to the first Web page, said query being in a first format;
    translating the query into a plurality of different formats;
    sending the query in the plurality of different formats over the Internet to a plurality of remote data repositories;
    receiving results over the Internet from the plurality of remote data repositories;
    translating the received results into results in the first format; and
    sending the results in the first format over the Internet to the client's browser.

33. The method of claim 32 wherein said remote data repositories include biology information.

34. The method of claim 32 wherein said remote data repositories include at least one of the following databases: ACeDB, SolGenes, Entrez, PIR, PDB, GenBank, and the WBG.

35. The method of claim 32 wherein the remote data repositories are genome databases.

36. The method of claim 32 wherein said first format is HTML.

37. The method of claim 32 further comprising:
    maintaining a data store on said server for a user of said client workstation.

38. The method of claim 37 wherein at least a portion of said plurality of results from the plurality of remote data repositories are kept in said data store.

39. The method of claim 37 wherein at least a portion of said translated results in the first format are kept on said data store.

40. An informatics system for managing users' access to a plurality of remote data repositories from a plurality of user-workstations connected to a server over a network, said informatics system comprising:
    a client-communicating program on said server for sending messages to and receiving messages from a client application on one of said plurality of user-workstations, said messages including a query request for information, said query request being in a first format;
    a query-translator program on said server and connected to receive said request in said first format from the client-communicating program, said query-translator program having a plurality of translation modules, each of said plurality of translation modules adapted to translate said query request from said first format into a query message to be submitted to one of the remote data repositories, said query message being a format different from said first format;

a communication program on said server and connected to the query-translator, said communication program adapted to send the translated query messages to the remote data repositories and receive results-messages therefrom; and a results-translator program on said server and connected to the communication program, to translate the results-messages received from the remote data repositories into results in said first format;

wherein said results-translator program is also connected to said client-communicating program to provide the translated response messages thereto.

41. The system of claim 40 wherein said results-translator program has a plurality of modules, each of said results-translator modules adapted to translate results-messages from one of said remote data repositories into said first format.

42. The system of claim 41 wherein each of said translation modules translates said query request into a different format.

43. An informatics and computing system for managing users' access to remote application programs from a plurality of user-workstations connected to a server over a network, said informatics system comprising:

a client-communicating program on said server for sending messages to and receiving messages from a client application on one of said plurality of user-workstations, said messages including a command request for executing computation, said command request being in a first format;

a command-translator program on said server and connected to receive said command request in said first format from the client-communicating program, said command-translator program having a plurality of translation modules, each of said plurality of translation modules adapted to translate said command request from said first format into a command message to be submitted to one or more of said remote application programs, said command message being a format different from said first format;

a communication program on said server and connected to the command-translator, said communication program adapted to send the translated command message to the remote application program and receive results-messages therefrom; and a results-translator program on said server and connected to the communication program, to translate the results-messages received from the remote application program into results in said first format;

wherein said results-translator program is also connected to said client-communicating program to provide the translated response messages thereto.

44. The system of claims 40 or 43 wherein said first format is HTML.

45. The system of claims 40 or 43 wherein said network includes the Internet.

46. The system of claims 40 or 43 further comprising:

a data store on said server, said data store for use by programs on said users' workstations.

47. The system of claim 46 wherein said data store includes at least a portion of said results-messages received.

48. The system of claim 46 wherein said data store includes at least a portion of said results in said first format.

49. The system of claim 46 wherein said client application is a browser.

* * * * *